US00PP20634P3

(12) United States Plant Patent
Rendle

(10) Patent No.: US PP20,634 P3
(45) Date of Patent: Jan. 5, 2010

(54) ***CORDYLINE* PLANT NAMED 'SUNRISE'**

(50) Latin Name: *Cordyline australis*
Varietal Denomination: Sunrise

(76) Inventor: Arthur Rendle, P.O. Box 113033, New Market, Auckland (NZ)

( * ) Notice: Subject to any disclaimer, the term of this patent is extended or adjusted under 35 U.S.C. 154(b) by 0 days.

(21) Appl. No.: 12/080,667

(22) Filed: Apr. 4, 2008

(65) Prior Publication Data

US 2009/0255020 P1 Oct. 8, 2009

(51) Int. Cl.
*A01H 5/00* (2006.01)

(52) U.S. Cl. ..... Plt./383
(58) Field of Classification Search ..... Plt./383
See application file for complete search history.

(56) References Cited

OTHER PUBLICATIONS

UPOV-ROM GTITM, Plant Variety Database, 2008/05, GTI Jouve Retrieval Software, citation for cordyline, 'Sunrise'.*

* cited by examiner

*Primary Examiner*—Susan B McCormick Ewoldt

(57) ABSTRACT

A new and distinct *Cordyline* cultivar named 'Sunrise' is disclosed, characterized by very stable, strongly variegated foliage of bright pink and burgundy and excellent performance in drought and high heat.

2 Drawing Sheets

Latin name of the genus and species: *Cordyline australis*.
Variety denomination: 'Sunrise'.

BACKGROUND OF THE INVENTION

The new cultivar is a product of a planned breeding program. The new variety originated from a cross pollination of the seed parent *Cordyline australis* 'Purple Tower,' an unpatented cultivar and the pollen parent *Cordyline australis* 'Torbay Dazzler,' also unpatented, made by the inventor during December 1995. It was discovered by the inventor, Arthur George Rendle, a citizen of New Zealand, in 1996 in New Plymouth, New Zealand.

Asexual reproduction of the new cultivar 'Sunrise' was first performed in Auckland, New Zealand by vegetative root cuttings. Subsequently 'Sunrise' has been reproduced by micropropagation and has shown that the unique features of this cultivar are stable and reproduced true to type through 20 generations.

SUMMARY OF THE INVENTION

The cultivar 'Sunrise' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'Sunrise' These characteristics in combination distinguish 'Sunrise' as a new and distinct *Cordyline* cultivar:

1. Strong, very bright pink stripe on the leaf.
2. Compact internodes.
3. Stable and consistent foliage variegation.

Plants of the new cultivar 'Sunrise' are similar to plants of the seed parent; *Cordyline australis* 'Purple Tower', in most horticultural characteristics, however, plants of the new cultivar 'Sunrise' have foliage with pink variegation, and a significantly finer leaf.

Plants of the new cultivar 'Sunrise' are similar to plants of the pollen parent; *Cordyline australis* 'Torbay Dazzler', in most horticultural characteristics, however, plants of the new cultivar 'Sunrise' have pink foliage variegation while the seed parent has green and yellow variegated foliage.

COMMERCIAL COMPARISON

'Sunrise' is best compared to the commercial variety *Cordyline australis* 'Southern Splendour,' U.S. Plant Pat. No. 19,102. Plants of the new cultivar 'Sunrise' are similar to plants of 'Southern Splendour' in most horticultural characteristics, however, plants of the new cultivar 'Sunrise' have foliage that is a much brighter, pink, of almost luminescent quality. Additionally, the red coloration in the foliage of 'Sunrise' is dark red, compared to pale red of 'Southern Splendour.'

BRIEF DESCRIPTION OF THE PHOTOGRAPH

Figure 1:
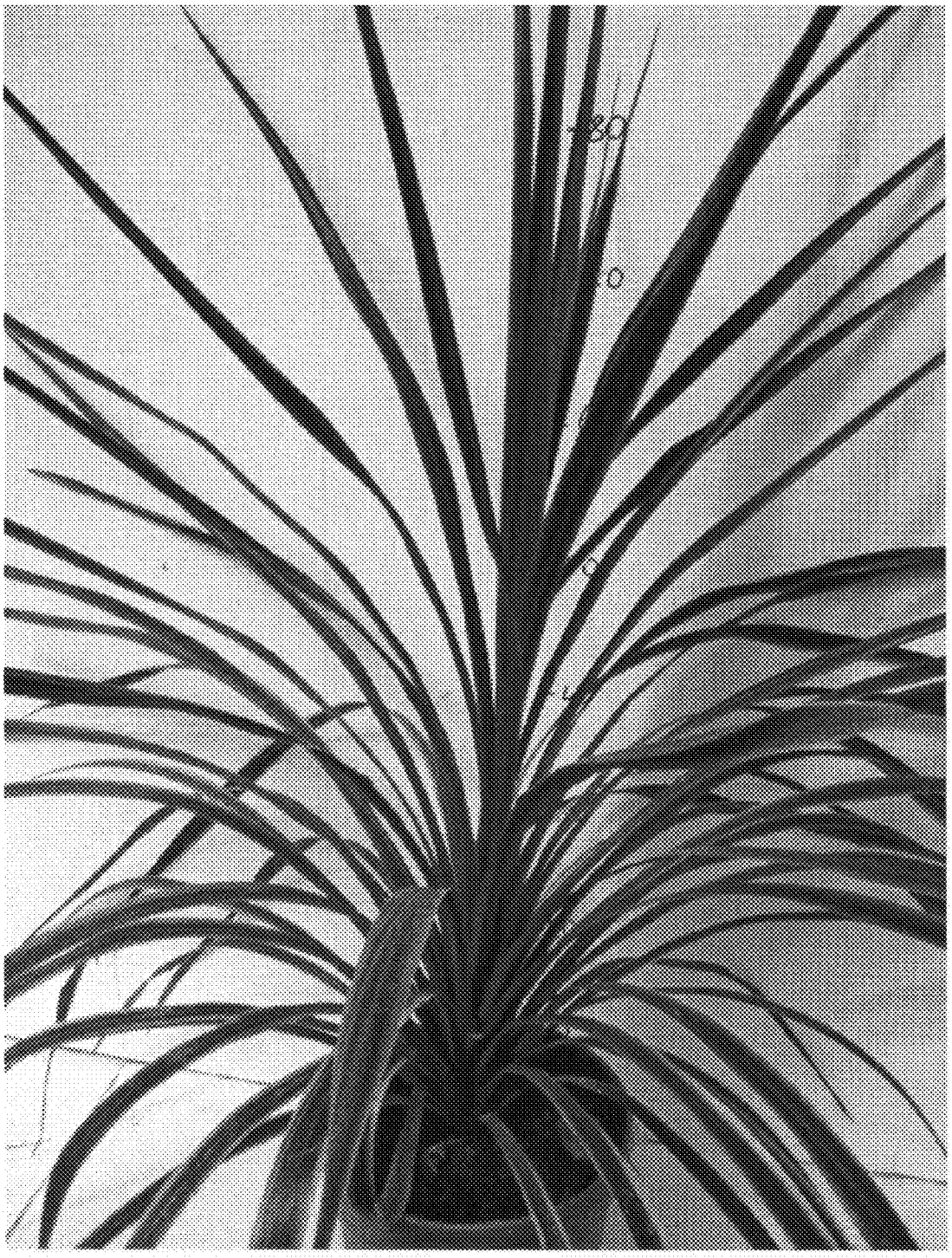

The accompanying photograph in FIG. 1 illustrates in full color a typical plant of 'Sunrise' grown in a greenhouse. This plant is approximately 15 months old, shown in a 5 liter pot.

Figure 2:
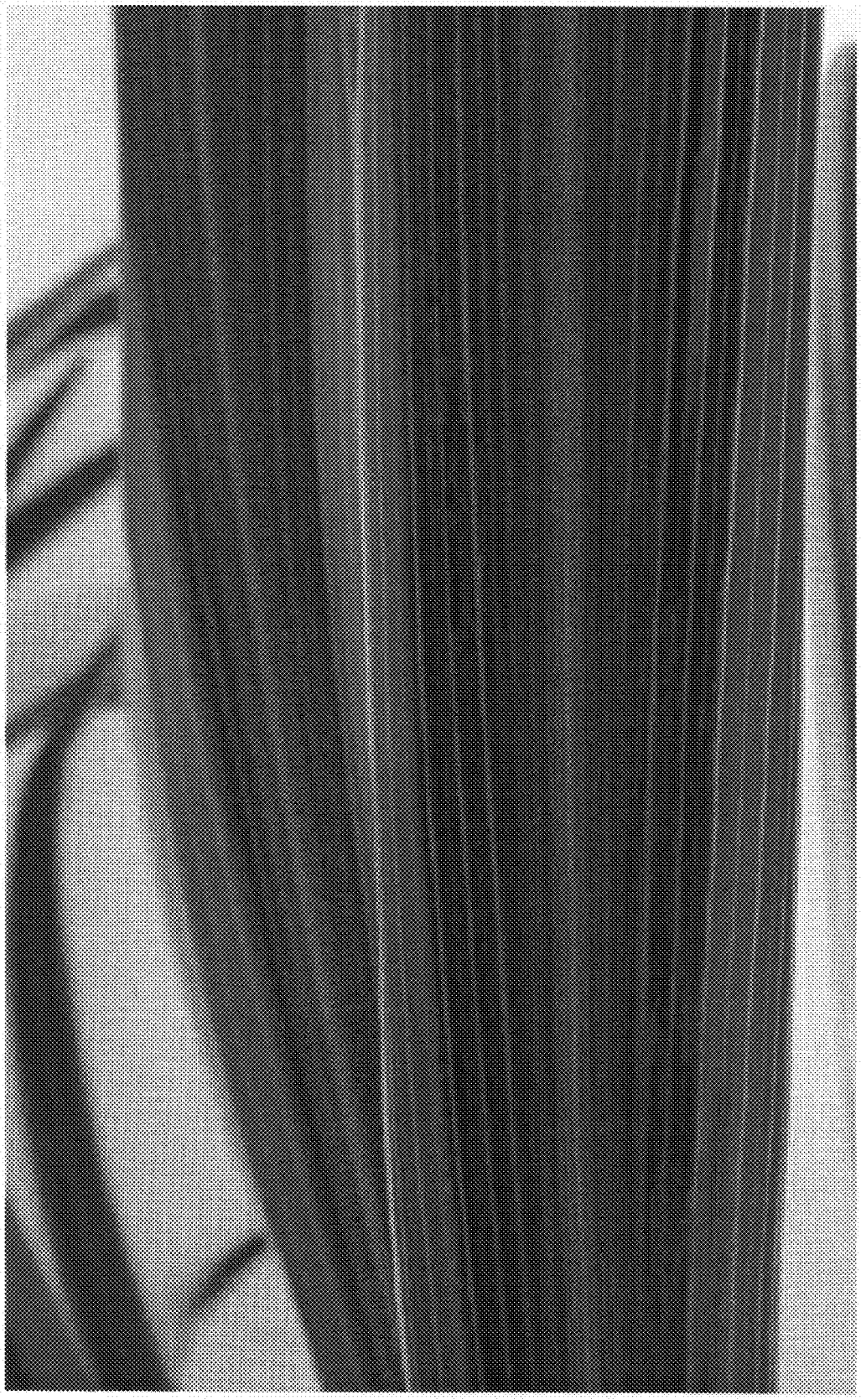

FIG. 2 illustrates in full color a typical leaf coloration of 'Sunrise.'

The photographs were taken using conventional techniques and although colors may appear different from actual colors due to light reflectance it is as accurate as possible by conventional photographic techniques.

DETAILED BOTANICAL DESCRIPTION

In the following description, color references are made to the Royal Horticultural Society Colour Chart except where general terms of ordinary dictionary significance are used. The following observations and measurements describe 'Sunrise' plants grown in a greenhouse in Las Pallas, Murcua, Spain during the Winter of 2006 through Spring of 2007. Temperatures ranged from 2° C. to 20° C. at night to 10° C. to 35° C. during the day. Measurements and numerical values represent averages of typical plant types.

Botanical classification: *Cordyline australis* cultivar 'Sunrise.'

PROPAGATION

Time to rooting: Approximately 6 weeks at approximately 15° C. soil temperature, 22° C. air temperature.

Root description: Fine, fibrous. No major tap root at the early stage.

PLANT

Growth habit: Upright perennial.

Height: Approximately 80 cm in a 5 liter pot. Approximately 300 to 400 cm after one year planted in the ground in a garden.

Blooming period: Not observed in commercial applications.

Plant Spread: Approximately 40 cm in a 5 liter pot. Approximately 100 to 150 cm after one year planted in the ground in a garden.

Growth rate: Slow to moderate. Generally slower than other *Cordyline australis* varieties.

Branching characteristics: Upright, non-branching.

Diameter of stem: Approximately 7 cm.

Number of leaves per stem: Approximately 200 .

Age of plant described: Approximately 15 months.

FOLIAGE

Leaf:

*Arrangement.*—Whorled.

*Average length.*—Approximately 60 cm.

*Average width.*—Approximately 1.5 cm near the base. Approximately 2.5 cm at the widest part of the leaf.

*Shape of blade.*—Linear.

*Apex.*—Highly acute, but, not sharp.

*Margin.*—Entire.

*Texture of top surface.*—Smooth, glossy.

*Texture of bottom surface.*—Smooth, leathery.

*Leaf internode length.*—2 mm.

*Color.*—Youngfoliage upper side: Variegated leaves, margins are near RHS Red 53C and Red 54A. Central rib area near RHS Grey-Brown 199A and 200B. Occasional stripes of Red 54A. Young foliage under side: Variegated leaves, margins are near RHS Red 53C and Red 54A. Central rib area near RHS Grey-Brown 1 99A and 200B. Occasional stripes of Red 54A. Mature foliage upper side: Variegated leaves, margins are near RHS Red 53C. Central rib area near RHS Grey-Brown 199A and 200B. Occasional stripes of Red 54A. Mature foliage under side: Variegated leaves, margins are near RHS Red 53C. Central rib area near RHS Grey-Brown 199A and 200B. Occasional stripes of Red 54A..

*Venation.*—Type: Linear Venation coloration: Not visible due to variegation in foliage.

Petiole: Not present

FLOWER

Flowering has not been observed to date, and is not commercially important in this cultivar.

OTHER CHARACTERISTICS

Disease resistance: Neither resistance nor susceptibility to diseases or pests has been observed in this variety.

Drought tolerance and cold tolerance: Hardy to −5° C. Tolerates temperatures above 40° C. Excellent drought tolerance. In a garden setting, 'Sunrise' can tolerate a minimum of 3 to 4 weeks without water undamaged.

Fruit/seed production: Not observed.

What is claimed is:

1. A new and distinct cultivar of *Cordyline* plant named 'Sunrise' as herein illustrated and described.

* * * * *